United States Patent [19]
Chedid et al.

[11] Patent Number: 5,753,287
[45] Date of Patent: May 19, 1998

[54] FLAVORED POPPING CORN WITH LOW OR NO FAT

[75] Inventors: Lisa Chedid, Monmouth Junction; David P. Huang, Bound Brook; Pat Baytan, Bloomfield, all of N.J.

[73] Assignee: National Starch and Chemical Investment Holding Corporation, Wilmington, Del.

[21] Appl. No.: 719,039

[22] Filed: Sep. 24, 1996

[51] Int. Cl.⁶ ............................. A23L 1/0522; A23L 1/18
[52] U.S. Cl. ............................. 426/93; 426/102; 426/103; 426/241; 426/309; 426/578; 426/629
[58] Field of Search .......................... 426/102, 103, 426/241, 309, 578, 629, 93

[56] References Cited

U.S. PATENT DOCUMENTS

| | | | |
|---|---|---|---|
| 3,525,672 | 8/1970 | Wurzburg et al. | 195/31 |
| 4,767,635 | 8/1988 | Merritt et al. | 426/272 |
| 4,849,233 | 7/1989 | Hemker | 426/93 |
| 4,977,252 | 12/1990 | Chiu | 536/102 |
| 5,284,666 | 2/1994 | Graf | 426/309 |
| 5,456,921 | 10/1995 | Mateescu et al. | 424/465 |

OTHER PUBLICATIONS

N-TACK™, Technical Service Bulletin, National Starch and Chemical Company, Food Products Division.

*Primary Examiner*—Helen Pratt
*Attorney, Agent, or Firm*—Karen G. Kaiser

[57] ABSTRACT

A flavored and/or colored unpopped popcorn is prepared by use of an amylase-treated low viscosity starch. Such popcorn may be popped in a microwave oven without the use of added fat or oil. Not only is the caloric content decreased due to lack of added fat, but the resultant popcorn has improved volume and flavor and/or color retention compared to conventional flavored popcorn using fat or oil.

22 Claims, No Drawings

FLAVORED POPPING CORN WITH LOW OR NO FAT

BACKGROUND OF THE INVENTION

The present invention relates to flavored popping corn with low or no fat.

Freshly popped popcorn, with its characteristic aroma and taste, has long been a popular snack product, particularly when flavored. The availability of flavored popcorn has increased over recent years, both the pre-popped and the home-popped varieties. Included in these flavored popcorns are the microwavable popcorns in which the unpopped kernels are coated or packaged in an oil or fat which serves both to heat the popcorn and as a coating or carrier for added salt and/or other flavoring.

The majority of the currently existing procedures require oil or fat to adhere any flavor and/or color to the product which generally results in an oily, greasy texture and feel as well as a high caloric content. As oil-popped popcorn has become less desirable to consumers watching their caloric intake, the industry for lower calorie/lower fat popcorn products has increased.

Few flavored popcorns are available without added fat or oil. These are primarily produced using hot air poppers. Hot air popped popcorn has the obvious advantage of producing popcorn which is neither greasy nor oily in taste and which is lower in calories. However, such popcorn generally is low in "popcorn flavor" and does not retain significant levels of added flavoring. Such low-flavored popcorn is not favored by consumers who tend to prefer the flavor of corn popped in conventional hot oil poppers or microwave ovens.

Non-fat based popcorn coatings are known in the art. For example, U.S. Pat. No. 4,767,635 discloses flavor-coated unpopped corn using a solution of an edible adhesive, such as gelatin, for use in hot air poppers. However, such coatings often result in significant loss of volume and flavor and/or color upon popping.

Surprisingly, it has now been discovered that a highly flavored popcorn may be produced without added oil or fat by using an edible coating comprising an amylase-treated low viscosity starch. Such flavored popcorn retains substantially all of its flavor and/or color. Further it pops to substantially the same volume as unflavored popcorn.

SUMMARY OF THE INVENTION

The present invention is directed to the preparation of a flavored and/or colored unpopped popcorn by use of an amylase-treated low viscosity starch. Such popcorn may be popped in a hot air popper or a microwave oven without the use of added fat or oil. Not only is the caloric content decreased due to lack of added fat, but the resultant popcorn has improved volume and flavor and/or color retention compared to conventional flavored popcorn using fat or oil.

An object of the present invention is to provide a flavored and/or colored popcorn which may be popped with substantially no added fat or oil.

Another object of the present invention is to provide a flavored and/or colored popcorn which may be popped with substantially no added fat or oil in a microwave oven.

Still another object of the present invention is to provide a flavored and/or colored popcorn which may be popped with substantially no added fat or oil and which has improved volume.

A further object of the present invention is to provide a flavored and/or colored popcorn which may be popped with substantially no added fat or oil and which has improved flavor and/or color retention.

These and other objects of the present invention will become apparent to one skilled in the art from the following detailed description and examples below.

DETAILED DESCRIPTION OF THE INVENTION

The present invention is directed to the preparation of a flavored and/or colored unpopped popcorn by use of an amylase-treated low viscosity starch. Such popcorn may be popped in a hot air popper or a microwave oven with substantially no added fat or oil. Not only is the caloric content decreased due to the decreased percent of fat, but the resultant popcorn has improved volume and flavor and/or color retention compared to conventional flavored popcorn using fat or oil.

The popcorn kernels to be used in this invention may be any variety of conventional unpopped popcorn kernels, including special hybrid corns or tougher varieties of corn which resist breakage upon mixing, in the coating method of this invention. Of particular importance are varieties which pop well in a microwave oven.

The base starch to be enzyme treated may include any cereal or root starch or flour. Examples of suitable materials include, but are not limited to, maize, rice, barley, wheat, sorghum, tapioca, potato, the waxy versions thereof, and the corresponding flours, particularly waxy starches, more particularly waxy corn starch. Converted, i.e., acid treated starches or chemically modified starches may also be used as the starting materials.

The starch is first steam cooked, particularly jet cooked. Jet cooking, as used herein, refers to slurrying the starch and heating the slurry to a temperature of from about 120° C. to about 170° C., in order to gelatinize substantially all of the starch. The steam cooking is generally carried out on a slurry at a solids level of from about 10 to about 40%, particularly about 20 to about 25% and a pH of about 4 to about 7, particularly about 4.5 to about 5.5, with a pressure greater than 60 psi in the cooking chamber.

The steam cooked starch is then enzymatically hydrolyzed using techniques known in the art and described, for example, in U.S. Pat. Nos. 3,525,672 to Wurzburg and 4,977,252 to Chiu. A single amylase is used, particularly at-amylase, P-amylase, or glucoamylase. Generally the enzyme treatment is carried out at a starch concentration level of about 10 to about 30%, particularly from about 18 to about 24%, depending upon the base starch used. The enzyme reaction is continued until the starch is sufficiently degraded to provide a viscosity of from about 7 to about 80 seconds, particularly from about 15 to about 60 seconds, more particularly from about 15 to about 30, measured at 19 % w/w solid concentration at room temperature using a standard funnel method (described in Example 1, supra).

Generally, the enzyme conversion will be carried out for time periods ranging from half an hour to 24 hours or more depending upon the temperature of the reaction, the type and concentration of enzyme used, and the starch concentration and viscosity of the reaction slurry. The enzyme reaction is terminated by raising the temperature to about 85° C. and maintaining that temperature for about ten minutes to fully deactivate the enzyme. Acid deactivation, as known in the art, can also be employed to deactivate the enzyme.

While it is preferred that the starch be steam cooked and subsequently hydrolyzed, it is also possible to obtain enzyme hydrolyzed starch for use herein by treating the granular starch with amylase and then steam cooking.

The resultant product is characterized by a dextrose equivalent (DE) of from about 1.5 to about 40, particularly from about 25 to about 35. Dextrose equivalent is defined as the reducing power of the hydrolysate. As each starch molecule has one reducing end, DE is inversely related to molecular weight. The DE of anhydrous D-glucose is defined as 100 and the DE of unhydrolyzed starch is virtually zero.

If waxy starch is employed as the base material, the final product can be used directly in liquid form wherein it will remain stable if stored under sterilized conditions. Alternatively, particularly in the case of non-waxy starches, the final product can be recovered in powdered form by conventional techniques, such as spray-drying, or drum-drying.

The final starch adhesive is characterized by its low viscosity and high degree of tackiness when wet so it can hold flavors and/or colors. It is also quick drying, providing a strong adhesive bond when dried, thus ensuring that the flavors and/or colors are retained on the popcorn kernels during later processing, packaging, transportation, storage, popping and consumer handling. Further, the starch adhesive is bland in taste so as not to interfere with the flavor of the popped corn and does not burn or otherwise deteriorate when used as a coating for popcorn kernels.

In order to use the resulting starch to bind flavor and/or color to popcorn kernels according to the present invention, the starch is ordinarily dissolved in water. The solution is prepared so that the solution concentration of the starch is from about 5 to about 50%, particularly above about 20%, more particularly above about 30%. An adherent-effective amount, for example from about 5 to about 50, particularly from about 5 to about 20, more particularly from about 8 to about 12% of the starch solution by weight of the unpopped kernels is then applied to the unpopped kernel surface using conventional techniques known in the art including, but not limited to, spraying such as by air atomization, pressure atomization, or rotating disc atomization, direct immersion, spray tumbling, and waterfall enrobing. Flavors and/or colors, particularly particulate flavors and/or colors, may then be immediately adhered to the coated kernels using conventional techniques known in the art including, but not limited to, drum tumbling, and electrostatics. It is important to affix the flavor and/or color before the starch solution dries. The amount of flavor and/or color added varies according to the flavor/color added and their intensity. In general, from about 0.5 to about 25, particularly from about 1 to about 8, more particularly from about 2 to about 5% of the flavor and/or color is added by weight of the unpopped kernels.

In the alternative, the flavor and/or color may be dissolved or dispersed directly in the starch solution. Once again, the amount of starch solution used is an adherent-effective amount. The resultant solution or slurry may then be applied directly onto the unpopped kernel using techniques known in the art including, but not limited to, spraying such as by air atomization, pressure atomization, or rotating disc atomization, direct immersion, spray tumbling, and waterfall enrobing.

Although either method of flavor application may be successfully carried out using this invention to prepare a flavored popcorn, the former method is preferable in that it generally provides a greater flavor impact upon consumption. Further, the two methods may be combined such that a flavored and/or colored solution may be used to coat the popcorn kernels and then a dry flavor and/or color may be adhered. Flavors include, but are not limited to, salt, butter flavoring, cheese powder, sugar, caramel flavoring, chili, Cajun spice, salsa, ranch seasoning, and sour cream and onion flavoring.

After the starch solution and flavor and/or color is applied to the unpopped kernel, the coated kernels are dried to about their original moisture; that is, the moisture prior to application of the starch solution. In general, a moisture range of from about 10 to about 15%, particularly from about 12 to about 14%, by weight is achieved. Drying may be conducted using any of the various means known in the art including application of low temperature heat or dry, hot air.

The moisture content of the kernels is important for proper popping, especially for optimum expansion of the corn. Although the instant invention requires that the coated kernels be dried, it has the advantage over many other coatings of using less water, thus requiring less drying. This is because the low viscosity of the starch solution allows for a relatively high concentration, up to about 50% by weight, to be easily applied by conventional means.

The resultant coated popcorn kernels may be popped by any means known in the art, particularly hot air popping or by microwaving, more particularly by microwaving. The instant flavored and/or colored popcorn is particularly suitable for microwave popping as it does not burn or otherwise deteriorate. Currently commercial microwave popcorns contain added fat and/or oil. Many non-fat alternatives to adhering the flavor and/or color burn during microwaving and therefore are not suitable for use in preparing such a product.

The instant adhesive is particularly suitable to producing a popcorn with a high volume. It is known in the art that many coatings, particularly non-fat based coatings such as gelatin, inhibit expansion of the popcorn kernels during popping, resulting in a denser texture and less volume. In comparison, the instant coated popcorn has a lighter, fluffier texture and a volume closer to that of uncoated popcorn.

The instant adhesive is also particularly suitable to producing a popcorn which retains a high percentage of the adhered flavor and/or color. Flavored and/or colored popcorns tend to lose their coatings during, processing, packaging, transportation, storage, popping and consumer handling. This is particularly true of flavors and colors which are adhered in particulate form. Such loss may be due to poor adhesion between the popcorn and the adhesive or between the adhesive and the flavor or color. The former is a problem of various gum adhesives which tend to flake off the popcorn. Poor adhesion is also a problem encountered when oil is used to adhere the flavoring or seasoning. In contrast, the instant adhesive may retain in excess of 95% of the flavor and/or color adhered prior to popping.

Another advantage of the instant invention is that the starch-based adhesive helps prevent the normally rapid uptake of moisture which can occur after popping causing the popcorn to become soggy and lose texture. This is especially important in a microwave popcorn as the bag traps moisture, exposing the popped corn to more moisture than in other conventional methods of popping corn.

EXAMPLES

The following examples are presented to further illustrate and explain the present invention and should not be taken as limiting in any regard.

Example 1

Funnel Viscosity

The starch dispersion to be tested is adjusted to 19% (w/w) measured by refractometer. The temperature of the dispersion is controlled at 22° C. A total of 100 ml of the starch dispersion is measured into a graduated cylinder. It is then poured into a calibrated funnel while using a finger to close the orifice. A small amount is allowed to flow into the graduate to remove any trapped air and the balance is poured back into the funnel. The graduated cylinder in then inverted over the funnel so that the contents draw (flow) into the funnel while the sample is running. Using a timer, the time required for the 100 ml sample to flow through the apex of the funnel is recorded.

The glass portion of the funnel is a standard 58° C., thick-wall, resistance glass funnel whose top diameter is about 9 to about 10 cm with the inside diameter of the stem being about 0.381 cm. The glass stem of the funnel is cut to an approximate length of 2.86 cm from the apex, carefully fire-polished, and refitted with a long stainless steel tip with is about 5.08 cm long with an outside diameter of about 0.9525 cm. The interior diameter of the steel tip is about 0.5952 cm at the upper end where is attached to the glass stem and about 0.4445 cm at the outflow end with the restriction in the width occurring at about 2.54 cm from the ends. The steel tip is attached to the glass funnel by means of a Teflon tube. The funnel is calibrated so as to allow 100 ml of water to go through in six seconds using the above procedure.

Example 2

Preparation of Popcorn Kernels a. A thirty percent (30%) solution of N-TACK® starch (commercially available from National Starch and Chemical Company) is prepared. 100 g of popcorn kernels are immersed in 50 g of the solution. The solution is decanted and 15 g salt are sprinkled over the coated kernels. The kernels are dried for twelve minutes at 250° F., breaking apart any kernels which are stuck together at three minute intervals. 10 g of the kernels are then placed in a 400 ml covered beaker and popped in a microwave oven for two minutes.

b. The above example, 2a, is repeated substituting powdered cheese flavoring for the salt.

c. The above example, 2a, is repeated substituting powdered butter flavoring for the salt.

Example 3

Preparation of Popcorn Kernels

A thirty percent solution of N-TACK® starch is prepared. 15 g of salt is dissolved in the solution. 100 g of popcorn kernels are immersed in 50 g of the solution. The solution is decanted and the kernels are dried for twelve minutes at 250° F., breaking apart any kernels which are stuck together at three minute intervals. 10 g of the kernels are then placed in a 400 ml covered beaker and popped in a microwave oven for two minutes.

Example 4

Taste Comparison

The popcorns of examples 2a and 3 are tasted. The popcorn of example 2a is clearly saltier than that of example 3.

Example 5

Spray Coating

A thirty percent (30%) solution of N-TACK® starch is prepared. 10 g of this solution are sprayed onto 100 g of popcorn kernels and 15 g salt are sprinkled over the coated kernels. The kernels are dried for twelve minutes at 250° F., breaking apart any kernels which are stuck together at three minute intervals. 10 g of the kernels are then placed in a 400 ml covered beaker and popped in a microwave oven for two minutes.

Example 6

Hot Air Popping a. The unpopped kernels of example 2a are popped in a commercially available home hot air popcorn popper.

b. The unpopped kernels of example 5 are popped in a commercially available home hot air popcorn popper.

Example 7

Hot Air Popping in a Manufacturing Environment 5 lbs. of the unpopped kernels of example 2a are popped in a National ICEE Air-Popt Model G popcorn machine (commercially available from National ICEE Corporation). After forty-five (45) minutes, essentially all of the kernels had popped without burning. Further, good volume was achieved with no apparent salt loss.

Example 8

Particulate Retention

Example 2a is repeated substituting a thirty percent PURITY GUM™ 59 modified food starch solution (a modified food starch commercially available from National Starch and Chemical Company), a ten percent gelatin solution, and a thirty percent gum arabic solution for the N-TACK® starch solution. Prior to popping the kernels, the beaker is weighed. After popping, the kernels, both popped and unpopped, are removed and the beaker is weighed. Percent salt retention is calculated as follows:

$$\text{salt lost} = \text{beaker weight after microwaving} - \text{beaker weight before microwaving}$$

$$\text{salt on microwaved kernels} = \text{salt adhered} * \frac{\text{coated kernels}}{\text{kernels} + \text{salt adhered}}$$

$$\% \text{ salt lost} = \frac{\text{salt lost}}{\text{salt on microwaved kernels}} * 100\%$$

The results are as follows:

| | N-TACK Starch | PURITY GUM™ 59 modified food starch | GELA-TIN | GUM ARABIC |
|---|---|---|---|---|
| KERNELS(g) (immersed in solution) | 100.06 | 100.04 | 100.10 | 100.10 |
| SALT ADHERED (g) (to kernels) | 6.74 | 6.15 | 4.58 | 5.69 |
| COATED KERNELS (g) (microwaved) | 10.40 | 10.03 | 10.06 | 10.33 |
| SALT LOST (g) | 0.00 | 0.39 | 0.00 | 0.12 |
| % SALT LOST | 0.00 | 67.14 | 0.00 | 21.60 |

As can be seen from the results above, not only does N-TACK® starch adhere the salt to the popcorn kernels better than PURITY GUM™ 59 modified food starch, gelatin or gum arabic, but N-TACK® starch also prevents salt from being lost during popping of the kernels.

Example 9

Volume Comparison

Using the popcorn kernels prepared in example 8, the volume of the popped kernels was measured. 15 g of kernels were popped. A 500 ml beaker was filled with poppy seeds and leveled off. The poppy seeds were removed. The popped sample was placed in the beaker and filled with poppy seeds. The excess poppy seeds were placed into a graduated cylinder and the volume read. The volumes of the popped samples are as follows:

|  | N-TACK Starch | PURITY GUM™ 59 modified food starch | GELA- TIN | GUM ARABIC |
|---|---|---|---|---|
| VOLUME (ml) | 163 | 159 | 149 | 150 |

As can be seen from the results above, the N-TACK® starch sample pops to the largest volume.

Example 10

Preparation of Popcorn Kernels Using a Combination of Adhesive Starches a. A 50:50 of N-TACK® corn syrup solids and PURITY GUM™ 59 modified food starch are used to prepare a thirty percent (30%) solution. 100 g of popcorn kernels are immersed in 50 g of the solution. The solution is decanted and 15 g salt are sprinkled over the coated kernels. The kernels are dried for twelve minutes at 250° F., breaking apart any kernels which are stuck together at three minute intervals. The kernels are then placed 10 g in a 400 ml covered beaker and popped in a microwave oven for two minutes.

We claim:

1. A popcorn product comprising a plurality of flavored and/or colored, unpopped popcorn kernels comprising unpopped popcorn kernels and a coating comprising an amylase-treated starch and at least one flavor and/or color, the amylase-treated starch being prepared by steam cooking starch and enzymatically hydrolyzing the cooked starch with a single amylase in an amount and for a sufficient time to achieve a funnel viscosity measured at 19% solids using a standard funnel of from about 7 to about 80 seconds and a dextrose equivalent of from about 1.5 to about 40.

2. The product of claim 1, wherein the starch is a waxy corn starch treated with an amylase selected from the group consisting of alpha-amylase, beta-amylase and glucoamylase to a funnel viscosity of from about 7 to about 80 seconds and a dextrose equivalent of from about 1.5 to about 40.

3. The popcorn product of claim 1, wherein the flavor is selected from the group consisting of salt, butter flavoring, cheese powder, sugar, caramel flavoring, chili, Cajun spice, salsa, ranch seasoning and sour cream and onion flavoring.

4. A popcorn product comprising the product of claim 1 which has been popped.

5. The popcorn product of claim 4, wherein the product has been popped using microwave energy.

6. The popcorn product of claim 4, wherein the product has been popped with substantially no added fat or oil.

7. The popcorn product of claim 4, wherein the product has been popped using a hot air popper.

8. A popcorn product prepared by the process which comprises:

a) dissolving an amylase treated starch in water to make a solution, wherein the starch is present in an amount of from about 30% to about 50% by weight, b) at least partially coating a plurality of unpopped popcorn kernels with an adhesive-effective amount of the solution, c) and adhering at least one flavor and/or color to the kernels, the amylase-treated starch being prepared by steam cooking starch and enzymatically hydrolyzing the cooked starch with a single amylase in an amount and for a sufficient time to achieve a funnel viscosity measured at 19% solids using a standard funnel of from about 7 to about 80 seconds and a dextrose equivalent of from about 1.5 to about 40.

9. The product of claim 8, further comprising d) drying the kernels to a moisture content of from about 13% to about 14%.

10. The product of claim 8, further comprising e) popping the popcorn kernels.

11. The product of claim 8, wherein the flavor is selected from the group consisting of salt, butter flavoring, cheese powder, sugar, caramel flavoring, chili, Cajun spice, salsa, ranch seasoning, and sour cream and onion flavoring.

12. The product of claim 10, wherein the popping is done using microwave energy.

13. The popcorn product of claim 10, wherein the popping is done with substantially no added fat or oil.

14. The product of claim 10, wherein the popping is done using a hot air popper.

15. A popcorn product prepared by the process which comprises:

a) dissolving an amylase treated starch in water to make a solution, wherein the starch is present in an amount of from about 30% to about 50% by weight, b) adding at least one flavor and/or color to the solution to form a mixture; and c) at least partially coating a plurality of unpopped popcorn kernels with an adhesive-effective amount of the mixture, the amylase-treated starch being prepared by steam cooking starch and enzymatically hydrolyzing the cooked starch with a single amylase in an amount and for a sufficient time to achieve a funnel viscosity measured at 19% solids using a standard funnel of from about 7 to about 80 seconds and a dextrose equivalent of from about 1.5 to about 40.

16. The product of claim 15, wherein the mixture is a slurry.

17. The product of claim 15, further comprising d) drying the kernels to a moisture content of from about 13% to about 14%.

18. The product of claim 15, further comprising e) popping the popcorn kernels.

19. The product of claim 18, wherein the popping is done using microwave energy.

20. The popcorn product of claim 18, wherein the popping is done with substantially no added fat or oil.

21. The product of claim 18, wherein the popping is done using a hot air popper.

22. The popcorn product of claim 15, wherein the process further includes (d) adhering at least one flavor and/or color to the at least partially coated kernels.

* * * * *